United States Patent [19]

Paciello et al.

[11] Patent Number: 5,689,010
[45] Date of Patent: Nov. 18, 1997

[54] PREPARATION OF HIGHER ALDEHYDES

[75] Inventors: Rocco Paciello, Bad Dürkheim; Franz Merger, Frankenthal; Michael Röper, Wachenheim; Heinz-Josef Kneuper, Mannheim, all of Germany

[73] Assignee: BASF Aktiengesellschaft, Ludwigshafen, Germany

[21] Appl. No.: 638,592

[22] Filed: Apr. 29, 1996

[30] Foreign Application Priority Data

May 4, 1995 [DE] Germany ............... 195 16 281.1

[51] Int. Cl.$^6$ .................... C07C 45/49
[52] U.S. Cl. ............... 568/451; 568/449; 568/454; 568/455
[58] Field of Search .................. 568/451, 449

[56] References Cited

U.S. PATENT DOCUMENTS 4,748,261  5/1988  Billig et al. .................. 556/404

FOREIGN PATENT DOCUMENTS

| 0058927 | 9/1982 | European Pat. Off. . |
| 058 927 | 9/1982 | European Pat. Off. . |
| 092 097 | 10/1983 | European Pat. Off. . |
| 366 089 | 5/1990 | European Pat. Off. . |
| 2125382 | 5/1971 | Germany . |
| 80/01691 | 8/1980 | WIPO . |
| WO08/01691 | 8/1980 | WIPO . |

OTHER PUBLICATIONS

Wolfgang Walter, "Lehrbuch der Organischen Chemie", 1988, pp. 200–201 and 206–209; 1980.
Krauch et al., "Reaktionen der Organischen Chemie", 1966, pp. 18–19.
J. Falbe, "New Syntheses with Carbon Monoxide", pp. 71–73 and 146–147; 1980.
Mieczynska et al., *J. of Molecular Catalysts*, vol. 80, 1993, pp. 189–200.

Primary Examiner—C. Warren Ivy
Assistant Examiner—Sreeni Padmanabhan
Attorney, Agent, or Firm—Keil & Weinkauf

[57] ABSTRACT

Aldehydes with a higher number of carbon atoms and high selection are prepared by reacting olefins, in particular from petrochemical refinery products, by a hydroformylation with aldol condensation using a mixed catalyst of rhodium-carbonyl-phosphines and Mannich catalyst.

19 Claims, No Drawings

PREPARATION OF HIGHER ALDEHYDES

The invention relates to the preparation of higher aldehydes. The invention particularly relates to the preparation thereof by hydroformylation of olefins and an aldol condensation.

Text books describe hydroformylation and the aldol condensation as separate processes, e.g. Bayer/Walter "Lehrbuch der organischen Chemie", S. Hirzel Verlag Stuttgart, 1988, 21st edition, pages 201, 206, 209. Page 206 mentions that catalysts of proven use for hydroformylation are the metals cobalt and rhodium, including their compounds. The aldol condensation is catalyzed by acids and bases (H. Krauch/W. Kunz "Reaktionen der organischen Chemie", Dr. Alfred Hüthig Verlag, Heidelberg, 3rd edition, 1966, page 18).

Catalysts described as advantageous in the patent literature for the aldol condensation of aldehydes are Mannich catalysts (EP-A-0 058 927, EP-A-0 092 097), comprising secondary amines and carboxylic acids. Two-stage separate processes are described in EP-A-0 366 089 and U.S. Pat. No. 4,748,261.

EP-A-0 366 089 discloses a three-stage process for preparing an alcohol with 10 carbon atoms, in which a $C_4$-olefin is subjected to a hydroformylation, aldol condensation and hydrogenation. A fraction with 4 carbon atoms, obtained in large quantity by thermal cracking or catalytic cracking of hydrocarbon oils, is hydroformylated, resulting in valeraldehydes (pentanals). The valeraldehydes obtained in this way are subjected to an aldol condensation to result in decenals, and the decenals obtained in this way are hydrogenated. The conditions for the hydroformylation are not particularly critical, but every conventional rhodium process and cobalt process can be used (page 3, line 56).

The aldol condensation is carried out using an aqueous alkaline solution such as NaOH, KOH or the like as catalyst, but it is also possible to use amines (page 5, line 32). The decenal mixture is subsequently subjected to hydrogenation.

A one-stage process for preparing higher aldehydes from olefins by hydroformylation with aldol condensation is described in the PCT application WO 80/01691. This discloses a process for preparing is aldehydes from α-olefins using rhodium-containing catalysts. Higher aldehydes can be prepared in a one-stage reaction in which at least one α-olefin with n carbon atoms, where n is 2 or a larger integer, is reacted in the liquid phase with a mixture of carbon monoxide and hydrogen in the presence of a rhodium-containing complex catalyst, free ligands and Lewis base to form an aldehyde with 2n+2 carbon atoms. WO 80/01691 describes that triphenylphosphine-based rhodium-containing catalysts are suitable. Suitable α-olefins are those with 2–12 carbon atoms. Suitable bases comprise, for example, inorganic bases such as KOH, and Lewis bases, e.g. organic bases such as triethanolamine.

A specific description is given of a process for preparing 2-propylheptanal based on 1-butene in the presence of Rh/PPh$_2$(CH$_2$CH$_2$SiMe$_3$)/KOH in diethylene glycol as solvent. The results of the continuous process (140° C., 20 bar, 95% conversion, >90% n content) are achieved in a 100 l autoclave. The disadvantages are a phase separation in the discharge from the reactor and an elaborate process for removing water from the solvent phase.

DE-A 21 25 382 describes a process for preparing 2-ethylhexanal based on propylene in the presence of Rh/triphenylphosphine/KOH in diethylene glycol as solvent. This catalyst system has the same disadvantages as those described above.

It is also reported in the literature that carboxylic acids reduce the rate of the low-pressure hydroformylation with rhodium (B. Cornils "New Synthesis with Carbon Monoxide", J. Falbe, Red., Springer-Verlag, 1980). In the Journal of Molecular Catalysis 80 (1993), page 189 there is also an investigation of the effect of carboxylic acids on the yield and selectivity of the hydroformylation of 1-hexene catalyzed by [Rh(acac)(CO)(PPh$_3$)], the result being that the reaction rate and the conversion of 1-hexene were reduced.

B. Cornils also describes, in "New Synthesis with Carbon Monoxide", a one-stage synthesis (oxation, aldolization and hydrogenation) of propylene to 2-ethylhexanol in the presence of a Co/PR$_3$ catalyst. A disadvantage is that only alcohols can be prepared.

It is an object of the present invention to improve the process for preparing higher aldehydes from olefins so that the disadvantages of the prior art are at least partly avoided in particular by considerably increasing the proportion of higher aldehydes in the reaction product, and carrying out the reactions at relatively low temperatures.

It is a specific object of the invention to find a process for preparing higher aldehydes which uses as starting material essentially directly the mixtures produced in the petrochemical industry.

We have found that this object is achieved by a process as defined in the claims. The invention thus relates in particular to a process for preparing aldehydes from olefins by a hydroformylation and an aldol condensation, wherein the olefins are reacted using a hydroformylation catalyst based on rhodium or cobalt with simultaneous use of a Mannich catalyst comprising secondary amines and carboxylic acids to form aldehydes.

It is advantageous in this connection to use a Mannich catalyst which has one or more of the following features:

a) the basic component used is a secondary amine of the general formula HNR$^1$R$^2$ where
   R$^1$ and R$^2$ are identical or different and each is alkyl which has 1 to 20, advantageously 1 to 12, preferably 6 to 12, carbon atoms and which can also be substituted by ether, hydroxyl, secondary, tertiary amino groups, in particular by one or two of these groups, aralkyl having 7 to 10 carbon atoms, cycloalkyl having 5 to 7 carbon atoms, and where
   R$^1$ and R$^2$ may also be with the adjacent nitrogen members of a heterocyclic, advantageously 5- to 7-membered ring, which may also contain other nitrogen atom and/or an oxygen atom and may be substituted by hydroxyalkyl or alkyl groups having 1 to 4 carbon atoms,
   specifically the compounds
   di-n-decylamine,
   piperidine,
   di-2-ethylhexylamine,
   dibenzylamine,
   and, in particular, RNHCH$_2$CH$_2$OH, where R can have the same meaning as R$^1$ and R$^2$ and is preferably HO—CH$_2$—CH$_2$—;

b) the acidic component used is an aliphatic mono, di- or polycarboxylic acid of the general formula R'CO$_2$H where R' is a hydrocarbon radical having 1 to 20 carbon atoms and, where appropriate, 1 to 5 further acidic groups, among these, specifically the compounds
   acetic acid,
   tridecanoic acid;

c) the Mannich catalyst is used at a concentration from 0.5% by weight to a concentration which suffices as high-boiling solvent.

Rhodium-carbonyl-phosphine complexes are used as hydroformylation catalyst and have one or more of the following features:

a) monophosphine or chelating phosphine ligands ($PR^1R^2R^3$) are used singly or in a mixture, where $R^1$, $R^2$ and $R^3$ are identical or different and comprise aliphatic radicals, preferably having 1 to 20 carbon atoms, or aromatic radicals, in particular
$PPh_3$ (triphenylphosphine)
$PPh_2$(Hex) (diphenylhexylphosphine)
$P(Oct)_3$ (trioctylphosphine)
BISBI (6,6'-bis(diphenylphosphinomethyl)-2,2'-biphenyl);

b) the molar ratio of phosphine (calculated as phosphorus equivalent) to rhodium used is from 1:1 to 1000:1, preferably 20:1 to 200:1 for monophosphine ligands, 2:1 to 6:1 for chelating phosphine ligands;

c) a rhodium-carbonyl complex is used, or a rhodium compound, preferably a halogen-free soluble rhodium compound, is used and then forms a carbonyl complex in situ.

Furthermore, a solvent which complies with one or more of the following points is used:

a) it is inert;

b) it is an alcohol having 1 to 20 carbon atoms, preferably 2-methylbutanol;

c) the aldehydes produced by the reaction of the particular olefin are used as solvents;

d) the high boilers produced by subsequent reactions of the particular aldehyde in the process are used.

The conversion of the olefins to aldehydes in the process according to the invention preferably takes place at from 30° to 150° C. under from 0.01 to 100 bar.

α-Olefins having 3 to 20 carbon atoms, in particular propylene, butenes or pentenes, are preferably used as starting materials.

An extremely favorable industrial variant is to use as starting material petrochemical raffinate II, with which $C_{10}$ aldehydes are prepared.

In this connection, raffinate II is a refinery product comprising $C_4$ hydrocarbons with the following components in the proportions indicated:

| | |
|---|---|
| isobutane | 5 to 15% by weight |
| n-butane | 15 to 30% by weight |
| isobutene | 0.1 to 5% by weight |
| 1-butene | 20 to 55% by weight |
| trans-2-butene | 15 to 30% by weight |
| cis-2-butene | 10 to 20% by weight |

When raffinate II is used as starting material, the products from $C_4$ olefins are, as outlined below,

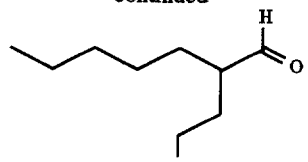

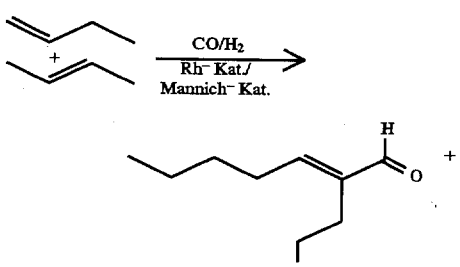

2-propylheptanals and 2-propylheptenals, which are hydrogenated to 2-propylheptanol. 2-Propylheptanol is a plasticizer alcohol which is preferentially used.

One advantage of the invention is that higher aldehydes can be obtained in good yields and selectivity in a one-stage process when rhodium-carbonyl-phosphine complexes are used with Mannich catalysts composed of a mixture of secondary amines and carboxylic acids as effective catalyst mixture. This advantage is particularly important on industrial use. Thus, surprisingly, the abovementioned opinion in the literature, that acids (acidic component of the Mannich catalyst) considerably inhibit the catalytic effect of the rhodium-carbonyl-phosphine complex is contradicted by the effect of the catalyst mixture according to the invention.

This invention not only improves a process for preparing higher aldehydes but also discloses a novel use of Mannich catalysts and a novel catalyst mixture for preparing higher aldehydes from olefins.

The higher aldehydes prepared according to the invention are converted in a subsequent hydrogenation into higher alcohols which are used for further processing to plasticizers.

The invention is described by means of the following examples which illustrate further preferred features of the invention.

EXAMPLES

Batchwise tests

All the batchwise tests were carried out as follows: $Rh(CO)_2(acac)$, phosphine ligand, aldol catalyst and solvent were placed in a 0.34 l autoclave (miniplant type, material HC) and raffinate II was injected into the closed autoclave. Raffinate II composition (% by weight):

| | |
|---|---|
| isobutane | 8.78% |
| n-butane | 26.5% |
| isobutene | 0.91% |
| 1-butene | 26.1% |
| trans-2-butene | 22.5% |
| cis-2-butene | 15.0% |

The liquid was vigorously stirred with a magnetic stirrer. The mixture was heated to the reaction temperature in 1.5 h. The required pressure was adjusted using $CO/H_2$ (1:1). During the reaction, the pressure in the reactor was maintained by further injection through a pressure controller. After the reaction time, the autoclave was cooled, decompressed and emptied. The reaction mixture was analyzed by gas chromatography (GC) with two internal standards and correction factors for $C_5$ and $C_{10}$ compounds.

Example 1

60.6 g (774 mmol of butenes) of raffinate II, 0.0666 g of $Rh(CO)_2(acac)$ (0.258 mmol), 32.5 g of $PPh_3$ (124 mmol), 3 g of di-n-decylamine (4.4% in the batch), 3 g of tridecanoic acid (4.4% in the batch) and 50 ml of 2-ethylhexanol ester (Texanol®) were subjected to a hydroformylation at 105° C. and 25 bar for 2.5 h. The aldehyde yield was 31.1%.

The selectivity for $C_5$ products was 45.8% and for $C_{10}$ products was 54.1%. The $C_5/C_{10}$ aldehyde ratio was 0.8. The proportion of n was 81.7%. (Proportion of n=(n-$C_5$+0.5× ($C_{10}$ from n-$C_5$+iso-$C_5$)+2×($C_{10}$ from n-$C_5$))/total aldehydes).

Comparative Example 2

The batch was carried out as in Example 1 but without Mannich catalyst. The aldehyde yield was 40.8%. The selectivity for $C_5$ products was 100%. The proportion of n was 82.4% (proportion of n=n-$C_5$/total aldehydes). Without the Mannich catalyst there is no aldol condensation ($C_{10}$ aldehyde=0).

Comparative Example 3

The batch was carried out as in Example 1, but the ligand/rhodium ratio (L/Rh) was 100:1 (mol/mol). The aldehyde yield was 35.6%. The selectivity for $C_5$ products was 46.8% and for $C_{10}$ products was 53.2%. The $C_5/C_{10}$ aldehyde ratio was 0.9. The proportion of n was 72.4%. The proportion of n can be controlled by the L/Rh ratio. However, the aldol condensation remains efficient.

Examples 4–8

The range of applications of the process according to the invention is illustrated below by some examples. However, these examples are by no means to be regarded as restrictive because good results are also obtained outside the range described.

Examples 4–5

Example 1 was repeated with the difference that PPh$_2$(Hex) (L/Rh=150) was used in 2-methylbutanol as solvent in the presence of 1.5% bis(2-ethylhexyl)amine at 120° C. and 45 bar for 10 h.

| Ex. | Acetic acid | Yield % | $C_5$ select. % | $C_{10}$ select. % | $C_5/C_{10}$ | n % |
|---|---|---|---|---|---|---|
| 4 | — | 63 | 83 | 11 | 7.4 | 30 |
| 5 | +1.5% | 53 | 63 | 37 | 1.7 | 37 |

It is evident that a carboxylic acid is advantageous for efficient aldol condensation.

Examples 6–8

Example 4 was repeated with the difference that 1.5% piperidine/1.5% acetic acid were used as Mannich catalyst. The effect of the temperature is evident from Examples 6–8.

| Ex. | Temperature °C. | Yield % | $C_5$ select. % | $C_{10}$ select. % | $C_5/C_1$$_0$ | n % |
|---|---|---|---|---|---|---|
| 6 | 120 | 62 | 52 | 48 | 1.1 | 47 |
| 7 | 100 | 46 | 35 | 65 | 0.5 | 63 |
| 8 | 80 | 27 | 30 | 70 | 0.4 | 74 |

It is evident that higher proportions of n can be obtained at lower temperatures. As the proportion of n increases the aldol condensation becomes more efficient. It is seen that Mannich catalysts can be used under very mild conditions.

Continuous test

Example 9

A continuous test was carried out in a 2.5 l autoclave with reciprocating agitator and internal cooling. After removal of the reaction product through a Sambay, the catalyst-containing bottom product was returned to the reactor. The rhodium concentration in the reactor was around 100 ppm. The ligand/rhodium ratio was 120:1 (mol/mol). The high boilers produced under the reaction conditions were used as solvent. CO/H$_2$ (ratio 1:1) was used. The pressure (20 bar) and the temperature (105° C.) were kept constant.

Raffinate II composition (% by weight):

| | |
|---|---|
| isobutane | 8.78% |
| n-butane | 26.5% |
| isobutene | 0.91% |
| 1-butene | 26.1% |
| trans-2-butene | 22.5% |
| cis-2-butene | 15.0% | a) The loading was 195 g/h raffinate II. After the system had started up the fluid discharge obtained was 70 g/h. The discharge contained 90% $C_5$ aldehydes with 86% n.

b) After the system had run in, a Mannich catalyst was added. Tridecanoic acid (2% of the total weight of solution in the system) and an equimolar amount of N-benzyl-2-phenylethylamine were used. While the loading remained the same the liquid discharge obtained was 42 g/h. The discharge contained 80% $C_5$+$C_{10}$ aldehydes with 90% n and a $C_5/C_{10}$ ratio of 1.3.

The feed conditions and the results of the tests are shown in the Table.

| Ex. No. | Hydroformylation catalyst | | Mannich catalyst | | Temp. (°C.) | Aldehyde yield (%) | $C_5$ selectivity (%) | $C_{10}$ selectivity (%) | $C_5/C_{10}$ ratio | Proportion of n |
|---|---|---|---|---|---|---|---|---|---|---|
| | Rh component | L (= phosphine) comp. | Base | Acid | | | | | | |
| | | | Batchwise tests | | | | | | | |
| 1 | Rh(CO)$_3$(acac) | PPh$_3$ | Di-n-decylamine | Tridecanoic acid | 105 | 32.1 | 45.8 | 54.1 | 0.8 | 81.7 |
| 2 | Rh(CO)$_3$(acac) | PPh$_3$ | | | 105 | 40.8 | 100 | | | 82.4 |
| 3 | Rh(CO)$_3$(acac) | PPh$_3$ L/Rh = 100:1 (mol/mol) | Di-n-decylamine | Tridecanoic acid | 105 | 35.4 | 46.8 | 53.2 | 0.3 | 72.4 |
| 4 | Rh(CO)$_3$(acac) | PPh$_2$(Hex) L/Rh = 150:1 (mol/mol) | Bis(2-ethylhexyl)- | | 120 | 63 | 83 | 11 | 7.4 | 30 |
| 5 | Rh(CO)$_3$(acac) | PPh$_2$(Hex) | Bis(2-ethylhexyl)- | Acetic acid | 120 | 53 | 63 | 37 | 1.7 | 37 |

-continued

| Ex. No. | Hydroformylation catalyst Rh component | L (= phosphise) comp. | Mannich catalyst Base | Acid | Temp. (°C.) | Aldehyde yield (%) | $C_5$ selectivity (%) | $C_{10}$ selectivity (%) | $C_5/C_{10}$ ratio | Proportion of n |
|---|---|---|---|---|---|---|---|---|---|---|
| 6 | $Rh(CO)_3(acac)$ | $PPh_2(Hex)$ L/Rh = 150:1 (mol/mol) | Piperidine | Acetic acid | 120 | 62 | 52 | 48 | 1.1 | 47 |
| 7 | $Rh(CO)_3(acac)$ | $PPh_2(Hex)$ L/Rh = 150:1 (mol/mol) | Piperidine | Acetic acid | 100 | 46 | 35 | 65 | 0.5 | 63 |
| 8 | $Rh(CO)_3(acac)$ | $PPh_2(Hex)$ L/Rh = 150:1 (mol/mol) | Piperidine | Acetic acid | 80 | 27 | 30 | 70 | 0.4 | 74 |
| Continuous test | | | | | | | | | | |
| 9a | $Rh_2(OAc)_6$ | $PPh_2$ L/Rh = 120:1 | | | 105 | 33 | 100 | 0 | | 86 |
| 9b | $Rh_2(OAc)_4$ | $PPh_2$ L/Rh = 120:1 | 2-Phenylethylamine | Tridecanoic acid | 105 | 17 | 56.5 | 43.5 | 1.3 | 90 |

Starting materials: raffinate II; acac = acetylacetonate; OAc = acetate; Ph = phenyl; Hex = hexyl

We claim:

1. A process for preparing aldehydes from olefins by a hydroformylation and an aldol condensation, wherein the olefins are reacted using a hydroformylation catalyst based on rhodium or cobalt with simultaneous use of a Mannich catalyst comprising secondary amines and carboxylic acids to form aldehydes.

2. A process as defined in claim 1, in which the Mannich catalyst has the following features:
   a) the basic component is a secondary amine of the formula $HNR^1R^2$ where
      $R^1$ and $R^2$ are identical or different and each is alkyl which has 1 to 20 carbon atoms and which can also be substituted by an ether, hydroxyl, secondary or tertiary amino or by an, aralkyl having 7 to 10 carbon atoms or cycloalkyl having 5 to 7 carbon atoms, and where
      $R^1$ and $R^2$ may also be with the adjacent nitrogen members of a heterocyclic ring, which may also contain another nitrogen atom or an oxygen atom or another nitrogen atom and an oxygen atom and may be substituted by hydroxyalkyl or alkyl groups having 1 to 4 carbon atoms;
   b) the acidic component is an aliphatic mono, di- or polycarboxylic acid of the formula $R'CO_2H$ where R' is a hydrocarbon radical having 1 to 20 carbon atoms and optionally, 1 to 5 further acidic groups;
   c) the Mannich catalyst is used at a concentration from 0.5% by weight to a concentration which suffices as high-boiling solvent.

3. A process as defined in claim 1, wherein rhodium-carbonyl phosphine complexes are used as hydroformylation catalyst and have one or more of the following features:
   a) monophosphine or chelating phosphine ligands $(PR^1R^2R^3)$ are used singly or a mixture, where $R^1$, $R^2$ and $R^3$ are identical or different and comprise aliphatic radicals or aromatic radicals;
   b) the molar ratio of phosphine (calculated as phosphorus equivalent) to rhodium used is from 1:1 to 1000:1 for monophosphine ligands, 2:1 to 6:1 for chelating phosphine ligands;
   c) a rhodium-carbonyl complex is used, or a rhodium compound is used and then forms a carbonyl complex in situ.

4. A process as defined in claim 2, wherein rhodium-carbonylphosphine complexes are used as hydroformylation catalyst and have one or more of the following features:
   a) monophosphine or chelating phosphine ligands $(PR^1R^2R^3)$ are used singly or in a mixture, where $R^1$, $R^2$ and $R^3$ are identical or different and comprise aliphatic radicals or aromatic radicals;
   b) the molar ratio of phosphine (calculated as phosphorus equivalent) to rhodium used is from 1:1 to 1000:1 for monophosphine ligands, 2:1 to 6:1 for chelating phosphine ligands;
   c) a rhodium-carbonyl complex is used or a rhodium compound is used and then forms a carbonyl complex in situ.

5. A process as defined in claim 1, wherein a solvent complying with one or more of the following points is used for the reactions:
   a) it is inert;
   b) it is an alcohol having 1 to 20 carbon atoms;
   c) the aldehydes produced by the reaction of the particular olefin are used as solvents;
   d) the high boilers produced by subsequent reactions of the particular aldehyde in the process are used.

6. A process as defined in claim 2, wherein a solvent complying with one or more of the following points is used for the reactions:
   a) it is inert;
   b) it is an alcohol having 1 to 20 carbon atoms;
   c) the aldehydes produced by the reaction of the particular olefin are used as solvents;
   d) the high boilers produced by subsequent reactions of the particular aldehyde in the process are used.

7. A process as defined in claim 3, wherein a solvent complying with one or more of the following points is used for the reactions:
   a) it is inert;
   b) it is an alcohol having 1 to 20 carbon atoms;
   c) the aldehydes produced by the reaction of the particular olefin are used as solvents;
   d) the high boilers produced by subsequent reactions of the particular aldehyde in the process are used.

8. A process as defined in claim 1, wherein the following conditions are adjusted for converting the olefins into aldehydes:
   Temperature: 30°–150° C.
   Pressure: 0.01–100 bar.

9. A process as defined in claim 1, wherein α-olefins having 3 to 20 carbon atoms, are used as olefins.

10. A process as defined in claim 1, wherein raffinate II is used as starting material.

11. A mixture of Mannich catalyst and rhodium hydroformylation catalyst.

12. A mixture as defined claimed in claim 11, wherein the Mannich catalyst has a composition as defined in claim 2.

13. A mixture as defined in claim 11, wherein the rhodium hydroformylation catalyst has a composition as defined in claim 3.

14. A mixture as defined in claim 11, wherein the Mannich catalyst has a composition as defined in claim 2 and the rhodium hydroformylation catalyst has a composition as defined in claim 3.

15. A process as defined in claim 2, wherein the basic compound is selected from the group consisting of di-n-decylamine, piperidine, di-2-ethylhexylamine, dibenzylamine, and $RNHCH_2CH_2OH$, where R can have the same meaning as $R^1$ and $R^2$.

16. A process as defined in claim 2, wherein the acidic component is acetic acid, or tridecanoic acid.

17. A process as defined in claim 3, wherein the monophosphine or chelating phosphine ligands are selected from the group consisting of $PPh_3$ (triphenylphosphine), $PPh_2$(Hex) (dipehnylhexylphosphine), $P(Oct)_3$ (trioctylphosphine) and BISBI (6,6'-bis(diphenylphosphinomethyl)-2,2'-biphenyl).

18. A process as defined in claim 4, wherein the monophosphine ligands are selected from the group consisting of $PPh_3$ (triphenylphosphine), $PPh_2$(Hex) (dipehnylhexylphosphine), $P(Oct)_3$ (trioctylphosphine) and BISBI (6,6'-bis(diphenylphosphinomethyl)-2,2'-biphenyl.

19. A process as defined in claim 1, wherein the olefins are reacted with hydrogen and carbon monoxide.

\* \* \* \* \*